United States Patent [19]

Hall

[11] Patent Number: 5,405,604
[45] Date of Patent: Apr. 11, 1995

[54] CONCENTRATED MOUTHRINSE FOR EFFICIENT DELIVERY OF ANTIMICROBIALS

[75] Inventor: William G. Hall, Cincinnati, Ohio

[73] Assignee: The Procter & Gamble Company, Cincinnati, Ohio

[21] Appl. No.: 122,750

[22] Filed: Sep. 16, 1993

Related U.S. Application Data

[63] Continuation-in-part of Ser. No. 1,862, Jan. 8, 1993, abandoned, which is a continuation-in-part of Ser. No. 961,999, Oct. 16, 1992, abandoned.

[51] Int. Cl.⁶ .................... A61K 7/16; A61K 7/22
[52] U.S. Cl. ............................... 424/54; 424/49; 424/58
[58] Field of Search .................. 424/49–88, 424/

[56] References Cited

U.S. PATENT DOCUMENTS

| | | | |
|---|---|---|---|
| 3,507,955 | 4/1970 | Osipow | 424/54 |
| 3,560,608 | 2/1971 | Griebstein et al. | 424/49 |
| 3,591,675 | 7/1971 | Brilliant | 424/54 |
| 3,954,962 | 5/1976 | Prussin | 424/49 |
| 3,988,433 | 10/1976 | Benedict | 424/53 |
| 4,032,661 | 6/1977 | Rowsell et al. | 424/337 |
| 4,082,841 | 4/1978 | Pader | 424/50 |
| 4,136,163 | 1/1979 | Watson et al. | 424/54 |
| 4,146,499 | 3/1979 | Rosano | 252/186 |
| 4,152,418 | 5/1979 | Pader | 424/50 |
| 4,312,889 | 1/1982 | Melsheimer | 426/86 |
| 4,323,551 | 4/1982 | Parran, Jr. | 424/54 |
| 4,472,373 | 9/1984 | Ryan | 424/54 |
| 4,525,343 | 6/1985 | Raaf | 424/54 |
| 4,568,480 | 2/1986 | Thir et al. | 252/312 |
| 4,606,911 | 8/1986 | Hayashi et al. | 424/49 |
| 4,627,978 | 12/1986 | Lynch | 424/54 |
| 4,657,758 | 4/1987 | Goldemberg et al. | 424/49 |
| 4,663,154 | 5/1987 | Ryan | 424/54 |
| 4,666,708 | 5/1987 | Goldemberg et al. | 424/49 |
| 4,716,035 | 12/1987 | Sampathkumar | 424/52 |
| 4,719,100 | 1/1988 | Frosch | 424/49 |
| 4,824,661 | 4/1989 | Wagner | 424/52 |
| 4,835,002 | 5/1989 | Wolf et al. | 426/590 |
| 4,839,158 | 6/1989 | Michaels | 424/54 |
| 4,842,766 | 6/1989 | Blehm et al. | 252/309 |
| 4,919,918 | 4/1990 | Cole et al. | 424/44 |
| 4,923,685 | 5/1990 | Wuelknitz et al. | 424/54 |
| 4,961,923 | 10/1990 | Heyde | 424/49 |
| 4,971,785 | 11/1990 | Wilson et al. | 424/44 |
| 4,971,788 | 11/1990 | Tabibi et al. | 424/49 |
| 4,975,271 | 12/1990 | Dunn et al. | 424/49 |
| 4,992,259 | 2/1991 | Schiraldi et al. | 424/49 |
| 4,994,262 | 2/1991 | Charbonneaau et al. | 424/52 |
| 5,045,337 | 9/1991 | El-Nokaly et al. | 426/602 |
| 5,078,988 | 1/1992 | Lin et al. | 424/49 |
| 5,100,650 | 3/1992 | Carlin et al. | 424/52 |
| 5,130,122 | 7/1992 | Tabibi et al. | 424/49 |
| 5,143,720 | 9/1992 | Lopes | 424/55 |
| 5,145,664 | 9/1992 | Thompson | 424/49 |
| 5,154,915 | 10/1992 | Weber et al. | 424/54 |
| 5,188,822 | 2/1993 | Viccaro et al. | 424/52 |
| 5,190,915 | 3/1993 | Behan et al. | 512/2 |
| 5,229,103 | 7/1993 | Eagle et al. | 424/49 |
| 5,283,056 | 2/1994 | Chung et al. | 424/49 |
| 5,284,648 | 2/1994 | White et al. | 424/49 |
| 5,290,541 | 3/1994 | Yang | 424/49 |
| 5,290,542 | 3/1994 | Yang | 424/52 |
| 5,292,527 | 3/1994 | Konopa | 424/54 |
| 5,320,863 | 6/1994 | Chung et al. | 426/650 |

FOREIGN PATENT DOCUMENTS

| | | | |
|---|---|---|---|
| 776425 | 6/1972 | Belgium . | |
| 1081127 | 7/1980 | Canada | A61K 7/16 |
| 740248 | 6/1980 | U.S.S.R. | A61K 7/16 |
| 874061 | 10/1981 | U.S.S.R. | A61K 7/16 |

OTHER PUBLICATIONS

MER–FLU–AN, A mouthwash concentrate; packaging material and bottle.
Goldberg et al., Biofouling 3(3):193–198 (1991), Bacterial Desorption by Commercial Mouthwashes vs Two–Phase Oil:Water Formulations.

*Primary Examiner*—Shep K. Rose
*Attorney, Agent, or Firm*—David K. Dabbiere; Douglas C. Mohl; Jacobus C. Rasser

[57] ABSTRACT

Concentrated mouthrinse, methods of use and methods of manufacturing the mouthrinse for efficient delivery of antimicrobials wherein the composition is concentrated and substantially free of non-cationic surfactants.

14 Claims, No Drawings

CONCENTRATED MOUTHRINSE FOR EFFICIENT DELIVERY OF ANTIMICROBIALS

This is a continuation-in-part of application Ser. No. 001,862, filed on Jan. 8, 1993, now abandoned, which is a continuation-in-part of application Ser. No. 961,999, filed Oct. 16, 1992, now abandoned.

TECHNICAL FIELD

The present invention relates to a concentrated mouthrinse and methods of use and methods of making the same, wherein there is an efficient delivery of antimicrobials to the oral cavity thereby reducing oral bacteria, mouth malodor and further promoting oral health.

BACKGROUND OF THE INVENTION

Plaque is an organic mixture of living bacteria found in the mouth. The bacteria found in plaque can secrete acids, enzymes and microtoxins which can cause caries, oral malodor and periodontal diseases such as gingivitis. It has been discovered that the compositions of the present invention possess a unique ability to form a concentrated and aesthetically pleasing mouthrinse. This invention provides a system by which, upon dilution, a relatively low concentration of a germ-killing cationic antimicrobial agent can be efficiently delivered to the oral cavity. In combination with the delivery of the antimicrobial, it has also been discovered this mechanism efficiently delivers a flavoring agent. This discovery therefore provides, without the need for non-cationic suffactants, excellent taste and breath refreshment, and also efficient delivery of an antimicrobial agent providing effective germ killing activity, thereby promoting oral health.

The use of mouthrinses to reduce or eliminate the bacterial flora of the oral cavity has been recognized for some time. Examples of previous references include: U.S. Pat. No. 4,994,262, Feb. 19, 1991 to Charbonneau et al.; U.S. Pat. No. 4,923,685, May 8, 1990 to Wuelknitz et al.; U.S. Pat. No. 4,839,1.58, Jun. 13, 1989 to Michaels; U.S. Pat. No. 4,824,661, Apr. 25, 1989 to Wagner; U.S. Pat. No. 4,719,100, Jan. 12, 1988 to Frosch; U.S. Pat. No. 4,716,035, Dec. 29, 1987 to Sampathkumar; U.S. Pat. No. 4,606,911, Aug. 19, 1986 to Hayashi et al.; U.S. Pat. No. 4,525,343, Jun. 25, 1985 to Raaf; U.S. Pat. No. 4,323,551, Apr. 6, 1982 to Parran, Jr.; U.S. Pat. No. 4,3 12,889, Jan. 26, 1982 to Melsheimer; U.S. Pat. No. 4,152,418, May 1, 1979 to Pader; U.S. Pat. No. 4,082,841, Apr. 4, 1978 to Pader; U.S. Pat. No. 3,988,433, Oct. 26, 1976 to Benedict; U.S. Pat. No. 3,954,962, May 4, 1976 to Prussin; and U.S. Pat. No. 3,560,608, Feb. 2, 1971 to Griebstein et al.

In addition to the compositions set forth in the above-mentioned U.S. Patents, several additional references disclose mouthrinses for use in the oral cavity. See for example: Belgian Patent 776,425, published Jun. 8, 1972, to Imperial Chemical Industries Limited; Canadian Patent 1081-127, published July 8, 1980; Japanese Kokai 54008-713, published Jan. 23, 1979; Japanese Kokai 49007-440, published Jan. 23, 1974; Soviet Union Patent 874-061, published Oct. 25, 1981 to Krasd Perfume Works and Soviet Union Patent Application 740-248, published Jun. 6, 1980 to Mosc Svoboda Cosmetics (similar to U.S. Pat. No. 3,591,675, Jul. 6, 1971 to Brillant).

While antimicrobials have long been used in oral mouthrinses, there is still a need for additional formulations which provide improved performance in combating oral disease along with increased user acceptance.

The present invention relates to compositions comprising certain solvents and cationic antimicrobial agents solubilized into a concentrated solution which is aesthetically pleasing. This mouthrinse is diluted with water to provide a safe and effective means for reducing bacteria found in the oral cavity and further provides a signal of efficacy to users. Compared to the ready-to-use conventional mouthwashes and rinses, the antimicrobials and flavoring agents of the present invention are delivered more efficiently while employing similar concentrations.

It is therefore an object of the present invention to provide a concentrated and aesthetically pleasing mouthrinse which upon dilution delivers more effectively the antimicrobial and flavoring agents while employing concentrations of these ingredients similar to ready-to-use mouthwashes and rinses.

A further object of the present invention is to provide a safe and effective means of preparing a mouthrinse from the concentrated solution.

These objects and other objects will become more apparent from the detailed description that follows.

SUMMARY OF THE INVENTION

The present invention relates to compositions of non-carbonated, concentrated, oil-in-water emulsions suitable for use as oral mouthrinses, comprising:
(a) a safe and effective amount of a cationic antimicrobial agent;
(b) a safe and effective amount of a solvent suitable for use in the oral cavity;
(c) a safe and effective amount of a flavoring agent; and
(d) water wherein the pH of the composition is from about 5 to about 8 and wherein the composition is substantially free of anionic and non-ionic surfactants and wherein the said oil-in-water emulsion breaks upon dilution with greater than about 5% v/v of an aqueous solution. Methods of use are also disclosed.

All concentrations and ratios herein are by weight and all measurements are made at 25° C., unless otherwise specified.

DETAILED DESCRIPTION OF THE INVENTION

By "safe and effective amount" as used herein, means an amount sufficient to reduce oral bacteria and/or enhance such reduction while providing no adverse effects to the hard and soft tissues of the oral cavity.

By "substantially free of anionic surfactant" as used herein, means less than 0.05%, preferably less than 0.01% and most preferably less than 0.001% of an anionic surfactant. By "substantially free of non-ionic surfactant" as used herein, means an amount which will not substantially impair the activity of the cationic surfactant. Generally, this means the composition must contain less then about 0.5%, preferably less than 0.3% and most preferably less than 0.2% of the nonionic surfactant.

The compositions of this invention employ a cationic antimicrobial agent, a solvent or a mixture of solvents, a flavoring agent or mixture of flavoring agents and water. The concentrated mouthrinse is preferably clear. By "clear" as used herein does not mean colorless, but means substantially lacking the presence of particles of sufficient size to scatter visible light as detected visually.

At the time of usage, the concentrated mouthrinse is mixed with a desired amount of water. This mixing allows for phase separation immediately prior to use. Without being limited by theory, it is believed that this phase separation provides an efficient delivery of a sufficient level of antimicrobial agents, while allowing for optimal taste and aesthetics.

The amount of water added to the concentrated mouthrinse mixture must be high enough to result in the necessary phase change as described below. This phase change is conveniently observed by the user during

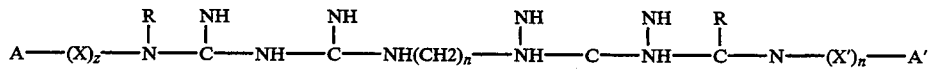

dilution and provides a visual signal alerting the consumer the composition is ready for use.

Without being limited by theory, it is believed during dilution, as the oil phase and aqueous phase separate, the flavoring oils which are highly water-insoluble become uniformly dispersed within the water phase of the ready-to-use mouthrinse. The antimicrobial of the present invention, due to its inherent properties having both a hydrophobic and hydrophylic moiety, resides primarily at the oil-water interface. This phase separation, where the oily phase is dispersed within the water phase of the diluted mouthrinse remains for several hours. However, eventually the oily phase will coalesce and form a separate layer. Therefore, it is undesirable to dilute more concentrate than will be immediately used.

The pH of the present concentrated compositions range from about 5.0 to about 8.0 with the preferred pH being from about 6.5 to about 7.0 with the most preferred pH being about 6.9. The essential, as well as optional components of the compositions of the present invention are described below.

ESSENTIAL INGREDIENTS

Cationic antimicrobial agents

The antimicrobials used in the compositions of the present invention can be any cationic antimicrobial agents such as quaternary ammonium compounds and substituted guanidines such as chlorhexidine and the corresponding compound alexidine. Mixtures of these cationic antimicrobials may also be used in the present invention.

Antimicrobial quaternary ammonium compounds include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, Jun. 3, 1980 to Bailey which is incorporated herein by reference. The pyridinium compounds are the preferred quaternary ammonium compounds, the most preferred being cetylpyridinium chloride or tetradecylpyridinium chloride. Quaternary ammonium antimicrobial agents are included in the present invention at levels of about 0.05% to about 10.0%, preferably from about 0.2% to 3.0%, more preferably from about 0.5% to about 3.0% and most preferably from about 0.5% to about 2.0%.

The substituted guanidines are also suitable for use in this invention. Bisbiguanide compounds, which are preferred for use in the present invention, are those having the generic formula:

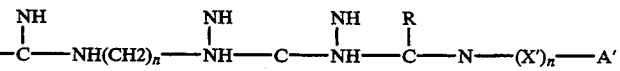

wherein A and A' can be either (1) a phenyl radical which optionally is substituted by an alkyl or alkoxy group containing from 1 to about 4 carbon atoms, a nitro group, or a halogen atom; (2) an alkyl group containing from about 1 to about 12 carbon atoms; or (3) alicyclic groups containing from about 4 to about 12 carbon atoms; wherein X and X' each represent an alkylene radical containing from about 1 to about 3 carbon atoms; wherein Z and Z' each can be either 0 or 1; wherein R and R' each represent either hydrogen, an alkyl radical containing from about 1 to about 12 carbon atoms, or an aralkyl radical containing from about 7 to about 12 carbon atoms; wherein n is an integer from 2 to 12 inclusive; wherein the polymethylene chain $(CH_2)_n$ may optionally be interrupted for example by oxygen, sulfur atoms or aromatic nuclei. The water soluble salts of the above compounds are especially preferred for use herein. Suitable water soluble salts include the chloride, the fluoride, and especially the acetate salt. The preferred substituted guanidine is chlorhexidine-[1,6-di(-N<5>-pchlorophenyl-N-diguanido)-hexane].

The substituted guanidine antimicrobials are generally used in the present compositions at a level of from about 0.05% to about 3.0%, preferably from about 0.5% to about 3.0% and most preferably from about 0.5% to about 2.0%.

Solvents or Solvent System

Another essential ingredient of the composition of the present invention is a solvent or solvent system such as those described in U.S. Pat. No. 5,141,961, Aug. 25, 1992 to Coapman, herein incorporated by reference. The solvent(s), which constitute the bulk of the present composition act as a carder for the flavoring oils. The solvent or solvent system solubilizes the flavoring oils in the concentrate and aids in dispersing, upon dilution with added water, all oil soluble components of the concentrated formulation thereby forming a uniformly dispersed mixture. The solvents most preferred for use in the present invention are: propylene glycol and polyethylene glycols or mixtures thereof. Propylene glycol and polyethylene glycols being most preferred.

Propylene glycol is well known in the art and available from any of a number of suppliers. Propylene glycol is miscible in all proportions and also has the ability to dissolve the flavoring agent of the present invention. Propylene glycol suitable for use in the present invention is obtainable from any number of sources such as Dow Chemical. Polyethylene glycols are also well known in the art and lower molecular weight species possess characteristics similar to propylene glycol.

Polyethylene glycols suitable for use in the present invention are the polyethylene glycols having an average molecular weight of less than or equal to 600, such as PEG 300 "Carbowax" supplied by Union Carbide.

Solvents comprise from about 30% to about 85%, preferably from about 35% to about 75% and most preferably from about 45% to about 60% of the concentrated form of the mouthrinse.

Water

Water is present in the concentrated composition of the present invention. Water comprises from about 10% to about 40%, preferably from about 18% to about 30% and most preferably from about 22% to about 26% of the oral compositions described herein. These amounts of water include the free water which is added, plus that amount which is introduced with other materials such as with sorbitol. The water, used in the present invention should preferably be deionized, distilled, free of organic impurities and bacteria and substantially free of metal ions.

Flavoring Agents

Another essential ingredient of the present invention is a flavoring agent or a mixture of compatible flavoring agents. Such flavoring agents are well known in the art. Suitable flavoring agents include: anise, cassia, clove, dihydroanethole, estragole, menthol, peppermint, oxanone, phenyl ethyl alcohol, sweet birch, thymol, eugenol, eucalyptol, wintergreen, spearmint, cinnamic aldehyde, menthone, alpha-ionone, ethyl vanillin, limonene, isoamylacetate, benzaldehyde, ethylbutyrate o and many others. In the herein described compositions the flavoring agents comprise from about 0.2% to about 9.0%, preferably from about 0.6% to about 4.0% and most preferably from about 2.0% to about 4.0% of the herein described composition.

OPTIONAL COMPONENTS

An optional ingredient useful in the present invention is a humectant or a mixture of compatible humectants. Humectants are well known in the art. In the present invention suitable humectants include the polyhydric alcohols such as xylitol, glycerin and sorbitol as well as other polyhydroxy alcohols and mixtures of these humectants. Although, it is feasible to use a single humectant, it is preferred o to incorporate a combination of humectants. Humectants provide from 0% to about 55%, and most preferably from about 15% to about 30% of the herein described invention. The preferred combination of humectants includes glycerin and sorbitol in a ratio of about 10:1 to about 1:4, and most preferably from about 3:1 to about 1:2.

Other optional components include, but are not limited to: coloring agents; sweeteners, including saccharin, dextrose, levulose, cyclamate and aspartate, along with many others; buffering systems such as benzoic acid and sodium benzoate, citric acid and sodium citrate and any other buffering system compatible with the invention's herein described essential components. Another optional component of the present invention is ethyl alcohol. Ethyl alcohol provides several functions when combined in the compositions of the present invention. Its inclusion can be, but is not limited to use as an additional antibacterial or as an astringent. Ethyl alcohol can be incorporated in the present invention at a level of less than about 40%, preferably less than about 10% and most preferably in concentrations of less than 2%.

Still another optional component of the present invention is a cooling agent such as those described in U.S. Pat. No. 4,136,163, Jan. 23, 1979, to Watson et al., U.S. Pat. No. 4,230,668, Oct. 28, 1980 to Rowsell et al. and U.S. Pat. No. 4,032,661, to Rowsell et al. all herein incorporated by reference. One particularly preferred cooling agent is N-ethyl-p-menthane-3-carboxamide (WS-3 supplied by Sterling Organics), taught by the above incorporated U.S. Pat. No. 4,136,163.

PROCESS OF PREPARING

The present invention to be effectively used as an antimicrobial mouthrinse should be prepared by the user just prior to use by adding an aqueous solution, preferably water to the concentrated oil-in-water emulsion or by adding the concentrated oil-in-water emulsion to water. Upon dilution, the oil-in-water emulsion breaks, leaving the diluted composition cloudy (or opaque). This generally occurs with the addition to the emulsion of greater than 5% v/v, preferably from about 10% and most preferably from about 20% of an aqueous solution. Therefore, after dilution, the resulting composition is not completely transparent. This transformation can be visually observed, or can be readily measured using a spectrophotometer. Any appreciable difference in the absorbance of light as between the undiluted concentrate and the diluted concentrate signifies the interaction and diffusion of light necessary to the invention, establishing the range of "cloudiness." No additional agitation or mixing energy is required to cause rapid dispersion, forming a uniformly dispersed mixture of the compositions antimicrobial(s), flavoring oil(s) and other ingredients. The dilution of the mouthrinse concentrate requires mixing the concentrate with water in a range of ratios from about 1:1 to about 1:100, preferably from about 1:2 to about 1:50, more preferably from about 1:5 to about 1:50 and most preferably from about 1:20 to about 1:50.

COMPOSITION USE

The present invention in its method aspect involves rinsing the oral cavity with a safe and effective amount of a mouthrinse prepared by the user by diluting the herein described concentrate with a suitable amount of water. Generally, an amount of at least about 0.01 grams of the antimicrobial becomes available by diluting the concentrate as described above and is effective in eliminating or reducing the bacterial flora residing within the oral cavity.

METHOD OF MANUFACTURING

The method of manufacturing the disclosed compositions of the present invention are common in the oral products area.

The following examples further describe and demonstrate preferred embodiments within the scope of the present invention. The examples are given solely for illustration, and are not to be construed as limitation of this invention as many variations thereof are possible without departing from its spirit and scope.

EXAMPLE I

A concentrated mouthrinse of the present invention is prepared by combining the following ingredients as described below. Also given is the dilution factor for diluting the concentrated composition.

| Dilution Ratio (concentrate:water) = 1:9 | |
|---|---|
| Cetylpyridinium Chloride | 0.5000% |
| Propylene Glycol | 55.0000% |
| Water | 25.8290% |
| Glycerin | 7.0000% |
| Sorbitol | 18.4000% |
| Flavor | 1.6600% |
| WS-3* | 0.3300% |
| Sodium Benzoate | 0.3200% |
| Benzoic Acid | 0.0210% |
| Sodium Saccharin | 0.7000% |
| Green Dye Solution (1%) | 0.2400% |

In a stainless steel or glass mixing tank containing the quantity of solvent, sequentially add the following ingredients dissolving each with agitation: flavor, cooling agent, benzoic acid, antibacterial, humectant(s), purified water, sodium benzoate, sweetening agent, and dye.

To the above concentrate a user adds 9 parts water. The diluted composition will become cloudy signaling the user the mouthrinse is ready for use. The user then rinses the oral cavity with approximately 20 ml of the diluted composition and expels the mouthrinse. This use reduces or eliminates the bacteria found in the oral cavity, preventing gingivitis and oral calamity. Substantially similar results are achieved when the above exemplified antimicrobial agent is replaced in whole or in part with Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride or any of the other herein described antimicrobial agents.

EXAMPLE II

| Dilution Ratio (concentrate:water) = 1:5 | |
|---|---|
| Cetylpyridinium Chloride | 0.3000% |
| Polyethylene Glycol | 45.0000% |
| Water | 23.5000% |
| Glycerin | 14.9990% |
| Sorbitol | 14.0000% |
| Flavor | 1.0000% |
| WS-3 | 0.2000% |
| Sodium Benzoate | 0.3200% |
| Benzoic Acid | 0.0210% |
| Sodium Saccharin | 0.4200% |
| Green Dye Solution (1%) | 0.2400% |

EXAMPLE III

| Dilution Ratio (concentrate:water) = 1:5 | |
|---|---|
| Cetylpyridinium Chloride | 0.3000% |
| Propylene Glycol | 45.0000% |
| Water | 23.5000% |
| Glycerin | 14.9990% |
| Sorbitol | 14.0000% |
| Flavor | 1.0000% |
| WS3 | 0.2000% |
| Sodium Benzoate | 0.3200% |
| Benzoic Acid | 0.0210% |
| Sodium Saccharin | 0.4200% |
| Green Dye Solution (1%) | 0.2400% |

EXAMPLE IV

| Dilution Ratio (concentrate:water) = 1:5 | |
|---|---|
| Tetradecylpyridinium Chloride | 0.3000% |
| Propylene Glycol | 60.0000% |
| Water | 18.0000% |
| Glycerin | 12.4990% |
| Sorbitol | 7.0000% |
| Flavor | 1.0000% |
| WS-3 | 0.2000% |
| Sodium Benzoate | 0.3200% |
| Benzoic Acid | 0.0210% |
| Sodium Saccharin | 0.4200% |
| Green Dye Solution (1%) | 0.2400% |

EXAMPLE V

| Dilution Ratio (concentrate:water) = 1:3 | |
|---|---|
| Cetylpyridinium Chloride | 0.2000% |
| Propylene Glycol | 35.0000% |
| Water | 16.0000% |
| Glycerin | 33.1490% |
| Sorbitol | 14.0000% |
| Flavor | 0.6600% |
| WS-3 | 0.1300% |
| Sodium Benzoate | 0.3200% |
| Benzoic Acid | 0.0210% |
| Sodium Saccharin | 0.2800% |
| Green Dye Solution (1%) | 0.2400% |

EXAMPLE VI

| Dilution Ratio (concentrate:water) = 1:29 | |
|---|---|
| Cetylpyridinium Chloride | 1.50% |
| Propylene glycol | 70.0% |
| Water | 23.5% |
| Flavor | 3.00% |
| Sodium Saccharin | 2.00% |

What is claimed is:

1. A non-carbonated, concentrated, oral composition in the form of an oil-in-water emulsion consisting essentially of:
   (a) from about 0.05% to about 10.0% of a cationic antimicrobial agent selected from the group consisting of quaternary ammonium compound;
   (b) from about 30% to about 85% of a solvent acting as a carrier for flavoring oil selected from the group consisting of propylene glycol, polyethylene glycol and mixtures thereof;
   (c) from about 0.2% to about 9.0% of a flavoring oil; and
   (d) from about 10% to about 40% water wherein the pH of the composition is from about 5 to 8 and wherein said concentrate of composition contains less than about 0.5% of anionic and nonionic surfactants and wherein said oil-in-water emulsion breaks upon dilution at the time of use into a cloudy or opaque composition with greater than about 5% v/v of an aqueous solution.

2. An oral composition according to claim 1 wherein the antibacterial compound is selected from the quaternary ammonium bacterial group consisting of cetylpyridinium chloride and tetradecylpyridinium chloride and mixtures thereof.

3. An oral composition according to claim 2 wherein the quaternary ammonium antibacterial compound is present at a level of from about 0.5% to about 3.0%.

4. An oral composition according to claim 3 wherein the antibacterial compound pound is cetylpyridinium chloride.

5. An oral composition according to claim 4 wherein the solvent is present at a level of from about 30% to about 75%.

6. An oral composition according to claim 5 wherein the solvent is present at a level of from about 30% to about 75%.

7. An oral composition according to claim 6 wherein the solvent is selected from the group consisting of propylene glycol and polyethylene glycol and mixtures thereof.

8. An oral composition according to claim 7 wherein the flavoring agent is from about 0.6% to about 4.0%.

9. An oral composition according to claim 8 which further comprises from about 5.0% to 55.0% of a humectant selected from the group consisting of glycerin and sorbitol and mixtures thereof.

10. An oral composition according to claim 9 which further comprises from about 0% to about 20% ethyl alcohol.

11. A process of preparing a mouthrinse comprising the steps of admixing the concentrated composition of claim 1 with water at a ratio of concentrate to water of from about 1:1 to about 1:100.

12. A process of preparing a mouthrinse comprising the steps of admixing the concentrated composition of claim 9 with water at a ratio of concentrate to water of about 1:2 to about 1:50.

13. A method of bacterial inhibition which comprises rinsing the oral cavity with a safe and effective amount of the composition of claim 1.

14. A method of bacterial inhibition which comprises rinsing the oral cavity
with a safe and effective amount of the composition of claim 9.

* * * * *